United States Patent [19]

Takeuchi et al.

[11] Patent Number: 5,747,614
[45] Date of Patent: May 5, 1998

[54] CATALYST FOR PRODUCING SYTRENIC POLYMER AND PROCESS FOR PRODUCING SYTRENIC POLYMER BY USING SAME

[75] Inventors: Mizutomo Takeuchi; Hajime Shouzaki; Norio Tomotsu, all of Ichihara, Japan

[73] Assignee: Idemitsu Kosan Co., Ltd., Tokyo, Japan

[21] Appl. No.: 569,121

[22] PCT Filed: Jul. 1, 1994

[86] PCT No.: PCT/JP94/01078

§ 371 Date: Jan. 2, 1996

§ 102(e) Date: Jan. 2, 1996

[87] PCT Pub. No.: WO95/01328

PCT Pub. Date: Jan. 12, 1995

[30] Foreign Application Priority Data

Jul. 2, 1993 [JP] Japan ................. 5-164529

[51] Int. Cl.$^6$ ............... A01J 31/00; C08F 4/44; C08F 4/02; B01J 37/00; B01J 31/00
[52] U.S. Cl. ............ 526/160; 526/943; 526/347.2; 526/170; 502/103; 502/117; 502/118; 502/123; 502/124; 502/132; 502/152; 556/43; 556/52; 556/53
[58] Field of Search .............. 534/10, 15; 556/43, 556/52, 53; 526/133, 160, 943; 502/103, 118, 123, 124, 129, 132, 152, 153, 154, 155, 162, 164, 202

[56] References Cited

U.S. PATENT DOCUMENTS

| | | | |
|---|---|---|---|
| 5,272,229 | 12/1993 | Tomotsu et al. | 526/115 |
| 5,329,031 | 7/1994 | Miyake et al. | 502/152 |
| 5,387,568 | 2/1995 | Ewen et al. | 502/152 |
| 5,430,001 | 7/1995 | Tomotsu et al. | 502/113 |
| 5,434,115 | 7/1995 | Yamada et al. | 502/152 |
| 5,461,128 | 10/1995 | Takeuchi et al. | 526/128 |
| 5,543,373 | 8/1996 | Winter et al. | 502/103 |
| 5,594,080 | 1/1997 | Waymouth et al. | 502/152 |

FOREIGN PATENT DOCUMENTS

| | | | |
|---|---|---|---|
| 0 426 637 | 10/1989 | European Pat. Off. | |
| 0 410 361 | 1/1991 | European Pat. Off. | |
| 0 417 313 | 3/1991 | European Pat. Off. | |
| 0 426 638 | 5/1991 | European Pat. Off. | |
| 0 427 696 | 5/1991 | European Pat. Off. | 502/117 |
| 0 427 697 | 5/1991 | European Pat. Off. | |
| 0 492 282 | 7/1992 | European Pat. Off. | |
| 0 505 890 | 9/1992 | European Pat. Off. | |
| 0 505 997 | 9/1992 | European Pat. Off. | |
| 0 543 022 | 5/1993 | European Pat. Off. | |
| 0 554 574 | 8/1993 | European Pat. Off. | |
| 0 591 841 | 4/1994 | European Pat. Off. | |
| 4-91095 | 3/1992 | Japan . | |
| 4-366108 | 12/1992 | Japan . | |
| 4-366109 | 12/1992 | Japan . | |
| 5-105712 | 4/1993 | Japan . | |

*Primary Examiner*—Glenn Caldarola
*Assistant Examiner*—J. Pasterczyk
*Attorney, Agent, or Firm*—Oblon, Spivak, McClelland, Maier & Neustadt, P.C.

[57] ABSTRACT

A catalyst for producing a styrenic polymer which comprises an (A) transition metal compound having one and only one π-ligand comprising only one indenyl group, said indenyl group bearing a substituent group at at least the 1-, 2-, or 3-positions of the indenyl ring, and wherein the transition metal is preferably at least one metal selected from the group consisting of titanium, zirconium, hafnium, niobium and tantalum, and optionally (B) at least one compound selected from the group consisting of ① an aluminoxane and ② an ionic compound comprising an anion that does not coordinate to the transition metal compound of component (A) in its cationic form, and a cation, and further optionally (C) a Lewis acid; and a process for producing a styrenic polymer using the catalyst.

14 Claims, No Drawings

CATALYST FOR PRODUCING SYTRENIC POLYMER AND PROCESS FOR PRODUCING SYTRENIC POLYMER BY USING SAME

TECHNICAL FIELD

The present invention relates to a novel catalyst for producing a styrenic polymer and a process for producing a styrenic polymer by using the same. More particularly, it pertains to a highly active catalyst for producing a styrenic polymer which contains a transition metal compound having a specific substituted indenyl group as a ligand and a process for efficiently producing a styrenic polymer having a high degree of syndiotactic configuration in its aromatic vinyl chain of the polymer.

BACKGROUND ART

Heretofore, styrenic polymers produced by the radical polymerization method or the like have an atactic configuration in stereostructure and are molded to various shapes by various molding methods such as injection molding, extrusion molding, blow molding, vacuum molding and cast molding, and they have been widely used as domestic electrical appliances, office machines, household goods, packaging containers, toys, furnitures, synthetic papers, and other industrial materials.

However, such styrenic polymers having atactic configuration have disadvantage that it is inferior in heat resistance and chemical resistance.

As opposed to the above, a styrene polymer having a syndiotactic configuration has a melting point higher than that of the conventional atactic polystyrene, and is expected to be used as a heat-resistant resin in various fields.

The present inventors have previously succeeded in developing such styrenic polymers having a syndiotactic configuration and disclosed a process for producing the same (see Japanese Patent Application Laid-Open Nos. 104818/1987, 187708/1987, 179906/1988, 241009/1988, 294705/1989 etc.).

Among the above-mentioned techniques, Japanese Patent Application Laid-Open No. 294705/1989 discloses a process for producing a styrenic polymer having a syndiotactic configuration by the use of a catalyst which comprises in combination a transition metal compound having an unsubstituted indenyl group as a π-ligand and an aluminoxane. However, the catalyst which comprises a transition metal compound having an unsubstituted indenyl group has not necessarily been sufficiently satisfactory with regard to its activity.

It view of the above, it is an object of the present invention to provide a novel and highly active catalyst for efficiently producing a styrene polymer having a high degree of syndiotactic configuration in its aromatic vinyl chain of the polymer, and at the same time, a process for producing a styrenic polymer by the use of said catalyst.

DISCLOSURE OF THE INVENTION

As a result of intensive research and investigation accumulated by the present inventors in order to attain the above-mentioned object, it has been found that a catalyst containing a transition metal compound having as a π-ligand, an indenyl group bearing at least one substituent group on the side of its five-membered ring, especially a catalyst comprising the above-mentioned transition metal compound and an aluminoxane and/or a specific ionic compound, or a catalyst comprising the above-mentioned transition metal compound and an aluminoxane and/or a specific ionic compound and a Lewis acid possesses a high activity and can efficiently produce an objective styrenic polymer having a high degree of syndiotactic configuration in its aromatic vinyl chain of the polymer. The present invention has been accomplished by the foregoing finding and information.

Specifically, the present invention provides a catalyst for producing a styrenic polymer which comprises a transition metal compound having as a π-ligand, an indenyl group bearing at least one substituent group on the side of its five-membered ring and a catalyst for producing a styrenic polymer which comprises (A) the aforesaid transition metal compound, (B) an aluminoxane and/or an ionic compound comprising a non-coordinating anion and a cation, and a (C) Lewis acid to be used as the case may be.

The present invention also provides a process for producing a styrenic polymer which comprises polymerizing an (a) styrenic monomer or an (a) styrenic monomer along with (b) at least one compound selected from olefins, diolefins and alkynes in the presence of the above-mentioned catalyst for producing a styrenic polymer.

THE MOST PREFERRED EMBODIMENT TO CARRY OUT THE INVENTION

The catalyst of the present invention for producing a styrenic polymer comprises a transition metal compound having as a π-ligand, an indenyl group bearing at least one substituent group on the side of its five-membered ring. A variety of such transition metals are available and exemplified by the compound represented by the general formula (I-a), $$RM^1X^1{}_aL^1{}_b \quad \text{(I-a)}$$

more specifically, the compound represented by the general formula (I-b);

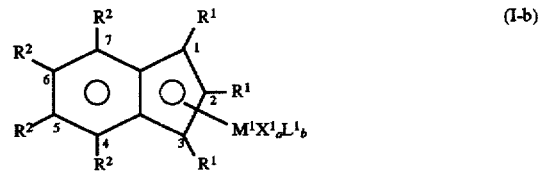

the compound represented by the general formula (II);

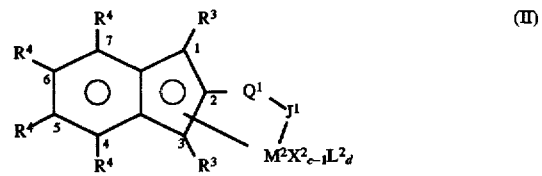

and the compound represented by the general formula (III), etc.

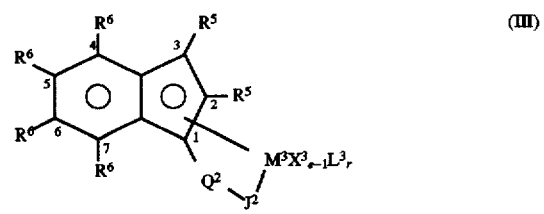

In the general formula (I-a), R stands for, as a π-ligand, an indenyl group bearing at least one substituent group on the side of its five-membered ring. In the general formula (I-a) and (I-b), M is a transition metal and examplified by titanium, zirconium, hafnium, lanthanidos, niobium and tantalum, among which titanium is particularly preferable; X is a oligand and is exemplified by a hydrogen atom, a hydrocarbon group having 1 to 20 carbon atoms, an aromatic hydrocarbon group having 6 to 20 carbon atoms, an alkoxyl group having 1 to 20 carbon atoms, an aryloxyl group having 6 to 20 carbon atoms, a thioalkoxyl group having 1 to 20 carbon atoms, a thioaryloxyl group having 6 to 20 carbon atoms, an amino group, an amide group, a carboxyl group, an alkylsilyl group, and a halogen atom, and a plurality of $X^1$ may be the same or different and bonded to each other through an arbitrary group; $L^1$ is a Lewis base; (a+b+1) is the valency of M; and b is 0, 1, 2 or 3.

In the general formula (I-b), $R^1$ and $R^2$ are each a hydrogen atom, a hydrocarbon group having 1 to 20 carbon atoms, especially an alkyl group having 1 to 20 carbon atoms, an aromatic hydrocarbon group having 6 to 20 carbon atoms, an alkoxyl group having 1 to 20 carbon atoms, an aryloxyl group having 6 to 20 carbon atoms, a thioalkoxyl group having 1 to 20 carbon atoms, a thioaryloxyl group having 6 to 20 carbon atoms, an amino group, an amide group, a carboxyl group, an alkylsilyl group, an indenyl group substituted with a halogen atom or the like with the proviso that at least one of $R^1$ is a group other than hydrogen atom; a plurality of $R^1$ may be the same or different; and a plurality of $R^2$ may be the same or different.

Specific examples of the R include 1-methylindenyl group; 2-methylindenyl group; 1-trimethylsilylindenyl group; 2-tert-butylindenyl group; 1,2-dimethylindenyl group; 1,3-dimethylindenyl group; 1,2,3-trimethylindenyl group; 1,2,3,4,7-pentamethylindenyl group; 1,4,5,6,7-pentamethylindenyl group; 1,3,4,5,6,7-hexamethylindenyl group; 1,2,3,4,5,6,7-heptamethylindenyl group; 1,2,3-trimethyl-4,7-dimethoxyindenyl group; and 1,2,3-trimethyl-4,7-difluoroindenyl group. Specific examples of $X_1$ include hydrogen atom, chlorine atom, bromine atom, iodine atom, methyl group, benzyl group, phenyl group, trimethylsilyl-methyl group; methoxy group, ethoxy group, phenoxy group, thiomethoxy group, thiophenoxy group, dimethylamino group, and diisopropylamino group.

As the transition metal compound represented by the foregoing general formula (I-a) or (I-b), there are preferably usable the transition metal compounds containing R and $X^1$ optionally selected from among those as exemplified above.

In the general formula (II), $R^3$ is the same as $R^1$ as defined above with the proviso that at least one of $R^3$ is a group other than hydrogen atom, and a plurality of $R^3$ may be the same or different; $R^4$ is the same as $R^2$ as defined above, and a plurality of $R^4$ may be the same or different; $M^1$, $X^2$, $L^2$, c and b are each the same as $M^1$, $X^1$, $L^1$, a and b, respectively; a plurality of $X^2$ may be the same or different and bonded to each other through an arbitrary group; $Q^1$ is a hydrocarbon group having 1 to 6 carbon atoms, an aromatic hydrocarbon group having 6 to 20 carbon group, a silylene group having 1 to 5 silicon atoms, a germylene group having 1 to 5 germanium group; and $J^1$ is an amide group, a phosphide group, oxygen atom, sulfur atom, an alkylidene group, or the like.

Further in the general formula (III), $R^5$ is the same as $R^1$ as defined above with the proviso that at least one of $R^5$ is a group other than hydrogen atom, and a plurality of $R^5$ may be the same or different; $R^6$ is the same as $R^2$ and a plurality of $R^6$ may be the same or different; $M^3$, $X^3$, $L^3$, e, f, $Q^2$ and $J^2$ are each the same as $M^1$, $X^1$, $L^1$, a, b, $Q^1$ and $J^1$, respectively; and a plurality of $X^3$ may be the same or different and bonded to each other through an arbitrary group.

As the transition metal compound represented by the above-mentioned general formula (II) or (III), mention is made of, for example, (tert-butyramide)(2,3-dimethylindenyl)-1,2-ethanediyltitanium dichloride; (tert-butyramide)(2,3-dimethylindenyl)-1,2-ethanediyldimethyltitanium; (tert-butyramide)(2,3-dimethylindenyl)-dimethylsilyltitanium dichloride; (tert-butyramide)(2,3-dimethylindenyl)-dimethylsilyldimethyltitanium; (tert-butyramide)(1,3-dimethylindenyl)-dimethylsilyltitanium dichloride; (tert-butyramide)(1,3-dimethylindenyl)-dimethylsilyldimethyltitanium; (tert-butyramide)(2,3,4,5,6,7-hexamethylindenyl)-dimethylsilyltitanium dichloride; (tert-butyramide)(2,3,4,5,6,7-hexamethylindenyl)-dimethylsilyldimethyltitanium; (tert-butyramide)(1,3,4,5,6,7-hexamethylindenyl)-dimethylsilyltitanium dichloride; (tert-butyramide)(1,3,4,5,6,7-hexamethylindenyl)-dimethylsilyldimethyltitanium; (2,3-dimethylindenyl)-1-ethane-2-oxatitanium dichloride; (2,3-dimethylindenyl)-1-ethane-2-oxadimethyltitanium; (phenylamide)(2,3-dimethylindenyl)-1,2-ethanediylzirconium dichloride; (tert-butyramide)(2,3-dimethylindenyl)-1,2-ethanediyldimethylzirconium; (tert-butyramide)(2,3-dimethylindenyl)-dimethylsilylzirconium dichloride; (tert-butyramide)(2,3-dimethylindenyl)-dimethylsilyldimethylzirconium; (tert-butyramide)(1,3-dimethylindenyl)-dimethylsilylzirconium dichloride; (tert-butyramide)(1,3-dimethylindenyl)-dimethyl-silyldimethylzirconium; (tert-butyramide)(2,3,4,5,6,7-hexamethylindenyl)-dimethylsilylzirconium dichloride; (tert-butyramide)(2,3,4,5,6,7-hexamethylindenyl)-dimethylsilyldimethylzirconium; (tert-butyramide)(1,3,4,5,6,7-hexamithylindenyl)-dimethylsilylzirconium dichloride; (tert-butyramide)(1,3,4,5,6,7-hexamethylindenyl)-dimethylsilyldimethylzirconium; (2,3-dimethylindenyl)-1-ethane-2-oxazirconium dichloride; (2,3-dimethylindenyl)-1-ethane-2-oxadimethylzirconium and the like.

The catalyst according to the present invention may contain one or not less than two kinds of the above-mentioned transition metal compounds.

The catalyst according to the present invention comprises a transition metal compound having as a π-ligand, an indenyl group bearing at least one substituent group on the side of its five-membered ring, and it is particularly preferable that the catalyst comprises (A) the above-mentioned transition metal compound and (B) an aluminoxane and/or an ionic compound comprising a non-coordinating anion and a cation, or that the catalyst comprises (A) the above-mentioned transition metal compound, (B) an aluminoxane and/or an ionic compound comprising a non-coordinating anion and a cation and (C) a Lewis acid.

The aluminoxane as the aforesaid component (B) is obtained by bringing an organoaluminum compound into contact with a condensation agent and is exemplified by chain aluminoxane represented by the general formula (IV)

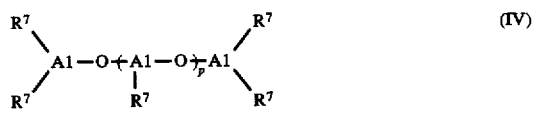

wherein $R^7$ is an alkyl group having 1 to 20 carbon atoms and p is a number of 0 to 50, preferably 5 to 30; and cyclic aluminoxane represented by the general formula (V)

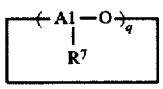

(V)

Wherein $R^7$ is as previously defined; and q is a number of 2 to 50, preferably 5 to 30.

Examples of the organoaluminum compound to be used as a starting material for the aluminoxane include a trialkylaluminum such as trimethylaluminum, triethylaluminum, triisobutylaluminum and a mixture thereof. Examples of the condensation agent is water as a typical one and optionally a material capable of undergoing a condensation reaction with the trialkylaluminum which material is exemplified by water adsorbed in an inorganic matter and diol.

Examples of the ionic compound comprising a non-coordinating anion and a cation as the component (B) include a compound represented by the general formula (VII) or (VIII)

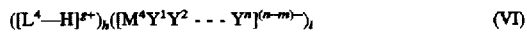 (VI)

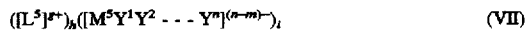 (VII)

wherein $L^5$ is $M^6$, $R^8R^9M^7$ or $R^{10}{}_3C$ as hereinafter described; $L^4$ is a Lewis base; $M^4$ and $M^5$ are each an element selected from Groups 5 to 15 of the Periodic Table and exemplified by B, Al, P, As and Sb; $M^6$ is an element selected from Groups 8 to 12 of the Periodic Table and exemplified by Ag and Cu; $M^7$ is an element selected from Groups 8 to 10 of the Periodic Table and exemplified by Fe, Co and Ni; $Y^1$ to $Y^n$ are each a hydrogen atom, dialkylamino group, alkoxy group, aryloxy group, alkyl group having 1 to 20 carbon atoms, aryl group having 6 to 20 carbon atoms, arylalkyl group, alkylaryl group, substituted alkyl group, organometalloid group or halogen atom and exemplified by dimethylamino group, diethylamino group, methoxy group, ethoxy group, butoxy group, phenoxy group, 2,6-dimethylphenoxy group, methyl group, ethyl group, propyl group, butyl group, octyl group, phenyl group, tolyl group, xylyl group, mesityl group, benzyl group, pentafluorophenyl group, 3,5-di(trifluoromethylphenyl)group, 4-tert-butylphenyl group, F, Cl, Br, I, pentamethylantimony group, trimethylsilyl group, trimethylgermyl group and diphenylboron group; $R^8$ and $R^9$ are each a cyclopentadienyl group, substituted cyclopentadienyl group, indenyl group, substituted indenyl group or fluorenyl group and exemplified by methylcyclopentadienyl group and pentamethylcyclopentadienyl group; $R^{10}$ is an alkyl group, aryl group or a substituted aryl group, may be the same or different and exemplified by a phenyl group, 4-methoxyphenyl group and 4-methylphenyl group; m is the valency of each of $M^4$ and $M^5$, indicating an integer from 1 to 7; n is an integer from 2 to 8; g is the ion valency of each of [L—H] and $[L^5]$, indicating an integer from 1 to 7; h is an integer of 1 or greater and i=(h×g)/(n−m).

Examples of the non-coordinating anion in the aforestated ionic compound include (tetraphenyl)borate; tetra (fluorophenyl)borate; tetrakis(difluorophenyl)borate; tetrakis(trifluorophenyl)borate; tetrakis(tetrafluorophenyl) borate; tetrakis(pentafluorophenyl)borate; tetrakis (trifluoromethylphenyl)borate; tetra(tolyl)borate; tetra (xylyl)borate; (triphenylpentafluorophenyl)borate; [tris (pentafluorophenyl)phenyl]borate and tridecahydride-7,8-dicarbaundecaborate. Examples of the cation in the above-mentioned ionic compound include triethyl ammonium; tributyl ammonium; N,N'-dimethylanilinium; N,N'-diethylanilinium; triphenylphosphinium; dimethylphenylphosphinium; 1,1'-dimethylferrocene; decamethylferrocene; silver (I); triphenyl carbenium; tritolylcarbenium; trimethoxyphenylcarbenium; [di(tolyl)phenyl]carbenium; [di(methoxyphenyl)phenyl]carbenium and [methoxyphenyl-di(phenyl)]carbenium.

The above-mentioned ionic compound can preferably be used by optionally selecting the non-coordinating anion and cation from among the above-exemplified examples and combining the selected ones.

In the catalyst of the present invention, the aluminoxane as the component (B) may be used alone or in combination with at least one other, the ionic compound also as the component (B) may be used alone or in combination with at least one other, and further at least one such aluminoxane may be used in combination with at least one such ionic compound.

Examples of the Lewis acid as the component (C) to be used when desired in the catalyst of the present invention include an organoaluminum compound, an organoboron compound, a magnesium compound, a zinc compound and a lithium compound.

Examples of the usable organoaluminum compound include the compound represented by the general formula (VIII)

 (VIII)

wherein $R^{11}$ and $R^{12}$ are each an alkyl group having 1 to 8 carbon atoms and may be the same or different ; $Z^1$ is a halogen atom; and r, s, t and u are numbers each satisfying the relations $0 < r \leq 3$, $0 < s \leq 3$, $0 \leq t < 3$, $0 \leq u < 3$ and $r+s+t+u=3$.

In the organoaluminum compound represented by the general formula (VIII), the compound wherein $t=u=0$ and $r=3$ is exemplified by trimethylaluminum, triethylaluminum, triisopropylaluminum, triisobutylaluminum and trioctylaluminum. Example of the compound corresponding to the case where $t=u=0$ and $1.5 \leq r < 3$, include diethylaluminum ethoxide, dibutylaluminum butoxide, diethylaluminum sesquiethoxide and dibutylaluminum sesquibutoxide; as well as partially alkoxylated alkylaluminum. Examples of the compound corresponding to the case where $s=t=0$ include diethylaluminum dichloride and dibutylaluminum dichloride ($r=2$); ethylaluminum sesquichloride and butylaluminum sesquichloride ($r=1.5$); and ethylaluminum dichloride and butylaluminum dichloride ($r=1$). Examples of the compound corresponding to the case where $s=u=o$ include diethylaluminum hydride and diisobutylaluminum hydride ($r=2$); and ethylaluminum dihydride and butylaluminum dihydride ($r=1$).

Examples of the organoboron compounds usable as the component (C) include the compound represented by the general formula (IX)

 (IX)

wherein $R^{13}$ is a hydrocarbon group having 1 to 20 carbon atoms, an aromatic hydrocarbon group having 6 to 20 carbon atoms, a substituted aromatic hydrocarbon group, hydrogen atom or a halogen atom, may be the same or different and specifically exemplified by a phenyl group, tolyl group, fluorophenyl group, trifluoromethylphenyl group, pentafluorophenyl group, fluorine atom, chlorine atom, bromine atom and iodine atom; $L^6$ is a Lewis base and exemplified by an ether compound such as diethyl ether and tetrahydrofuran and an amine compound such as pyridine; and v is an integer from zero (0) to 3.

Examples of the above-mentioned magnesium compound include a Grignard compound such as methylmagnesium bromide, ethylmagnesium bromide, phenylmagnesium bromide and benzylmagnesium bromide, an organomagnesium compound such as diethoxymagnesium and ethylbutylmagnesium and an inorganic magnesium compound such as magnesium chloride. In addition, mention may be made of a zinc compound exemplified by an organozinc compound such as diethylzinc and of a lithium compound exemplified by an organolithium compound such as methyllithium.

In the catalyst according to the present invention, the aforestated Lewis acid as the component (C) may be used alone or in combination with at least one other.

The catalyst according to the present invention, which comprises the components (A) and (B) or the components (A), (B) and (C), may be incorporated further with an other catalyst component. The blending ratio of each of the components varies depending upon various conditions and thus can not be determined unequivocally, but the molar ratio of the component (A) to the component (B) is usually selected in the range of preferably 1:1 to 1:10000, more preferably 1:1 to 1:1000 in the case of the component (B) being an aluminoxane, and it is usually selected in the range of preferably 0.1:1 to 1:0.1 in the case of the component (B) being an ionic compound. The molar ratio of the component (A) to the component (C) when used, is selected in the range of preferably 1:0.1 to 1:1000.

As a method for contact-mixing the components (A) and (B) and the component (C) to be used when desired, mention may be made of ① a method in which the component (C) is added to the contact mixture between the components (A) and (B) to form a catalyst, which is brought into contact with a monomer component to be polymerized; ② a method in which the component (A) is added to the contact mixture between the components (B) and (C) to form a catalyst, which is brought into contact with a monomer component to be polymerized; ③ a method in which the component (B) is added to the contact mixture between the components (A) and (C) to form a catalyst, which is brought into contact with a monomer component to be polymerized; ④ a method in which the components (A), (B) and (C) are each separately brought into contact with a monomer component to be polymerized; and ⑤ a method in which the catalyst prepared in the above-mentioned ①, ② or ③ is brought into contact with the contact mixture between the monomer component to be polymerized and the component (C).

The contact mixing among the components (A) and (B) and the component (C) to be used as desired can be carried out at a temperature in the range of –20° to 200° C., needless to say, at a polymerization temperature.

In the process according to the present invention, a styrenic polymer is produced by polymerizing, in the presence of the above-described catalyst, an (a) styrenic monomer alone or an (a) styrenic monomer along with (b) at least one compound selected from olefins, diolefins and alkynes.

Examples of the styrenic monomer as the aforesaid monomer component (a) include styrene, alkylstyrenes such as p-methylstyrene; m-methylstyrene; o-methylstyrene; 2,4-dimethylstyrene; 2,5-dimethylstyrene; 3,4-dimethylstyrene; 3,5-dimethylstyrene; and p-tertiary-butylstyrene; halogenated styrenes such as p-chlorostyrene; m-chlorostyrene; o-chlorostyrene; p-bromostyrene; m-bromostyrene; o-bromostyrene; p-fluorostyrene; m-fluorostyrene; o-fluorostyrene and o-methyl-p-fluorostyrene; organosiliconated styrenes, vinylbenzoic acid esters and divinylbenzene. Any of the above-mentioned styrenic monomer may be used alone or in combination with at least one other.

On the other hand, examples of the olefins as the aforesaid monomer component (b) include α-olefins such as ethylene; propylene; butene-1; pentene-1; hexene-1; heptene-1; octene-1; nonene-1; decene-1; 4-phenylbutene-1; 6-phenylhexene-1; 3-methylbutene-1; 4-methylpentene-1; 3-methylpentene-1; 3-methylhexene-1; 4-methylhexene-1; 5-methylhexene-1; 3,3-dimethylpentene-1; 3,4-dimethylpentene-1; 4,4-dimethylpentene-1; vinylcyclohexane; and vinylcyclohexene, halogen-substituted α-olefins such as hexafluoropropene; tetrafluoroethylene; 2-fluoropropene; fluoroethylene; 1,1-difluoroethylene; 3-fluoropropene; trifluoroethylene; and 3,4-dichlorobutene-1, cyclic olefins such as cyclopentene; cyclohexene; norbornene; 5-methylnorbornen; 5-ethylnorbornene; 5-propylnorbornene; 5,6-dimethylnorbornene; 1-methylnorbornene; 7-methylnorbornene; 5,5,6-trimethylnorbornene; 5-phenylnorbornene; 5-benzylnorbonene; and 5-vinylnorbornene. Examples of the diolefins include straight chain diolefins such as butadiene; isoprene; and 1,6-hexadiene, and cyclic diolefins such as norbornadiene; 5-ethylidenenorbornene; and dicyclopentadiene. Example of the alkynes include acetylene, methylacetylene, phenylacetylene and trimethylsilylacetylene. The above-mentioned monomer may be polymerized alone or in combination with at least one other monomer.

The polymerization method may be bulk polymerization method without specific limitation. The polymerization may be carried out in an aliphatic hydrocarbon solvent such as pentane, hexane and heptane, an alicyclic hydrocarbon solvent such as cyclohexane or an aromatic hydrocarbon solvent such as benzene, toluene, xylene and ethylbenzene. The polymerization temperature is not specifically limited but is usually 0° to 200° C., preferably 20° to 100° C. In the case where a gaseous monomer is employed, the partial pressure of the gaseous monomer is usually 300 kg/cm$^2$ or lower, preferably 30 kg/cm$^2$ or lower.

The styrenic polymer obtained in such a way has a high degree of syndiotactic configuration in its aromatic vinyl chain when it is contained in the polymer. In this case, a high degree of syndiotactic configuration in the aromatic vinyl chain of the styrenic polymer or styrenic compolymer signifies that its stereochemical structure is of high degree of syndiotactic configuration, i.e., the stereostructure in which phenyl groups or substituted phenyl groups as side chains are located alternately at opposite directions relative to the main chain consisting of carbon-carbon bonds. Tacticity is quantitatively determined by the nuclear magnetic resonance method ($^{13}$C-NMR method) using carbon isotope. The tacticity as determined by the $^{13}$C-NMR method can be indicated in terms of proportions of structural units continuously connected to each other, i.e., a diad in which two structural units are connected to each other, a triad in which three structural units are connected to each other and a pentad in which five structural units are connected to each other. "The styrenic polymers having such a high degree of syndiotactic configuration" as mentioned in the present invention usually means polystyrene, poly(substituted styrene), poly(vinyl benzoate), the mixture thereof, and copolymers containing the above polymers as main components, having such a syndiotacticity that the proportion of racemic diad is at least 75%, preferably at least 85%, or the proportion of racemic pentad is at least 30%, preferably at least 50%. Examples of the poly(substituted styrene) include poly(hydrocarbon group-substituted styrene)such as poly(methylstyrene), poly(ethylstyrene), poly(isopropylstyrene), poly(phenylstyrene) and poly(vinylstyrene); poly(halogenated styrene) such as poly(chlorostyrene), poly(bromostyrene), and poly(fluorostyrene); and poly(alkoxystyrene) such as poly(methoxystyrene) and poly(ethoxystyrene).

In the following, the present invention will be described in more detail with reference to examples, which however shall not be construed to limit the invention thereto.

The reaction in each of the synthesis examples was carried out in an atmosphere of dry nitrogen or in a stream of nitrogen unless otherwise noted.

Synthesis Example 1

Synthesis of 1,2,3,4,5,6,7-heptamethylindenyltianium trichloride (Compound A)

(1) Synthesis of 2,3,4,5,6,7-hexamethylindane-1-one

Aluminum trichloride in an amount of 58.7 g (440 mmol) was suspended in 300 mL (milliliter) of dried carbon disulfide (dried and distilled on calcium hydride) and was brought to an ice-cooling temperature. Then, 47.4 g (400 mmol) of tigloyl chloride was mixed with 53.7 g (400 mmol) of tetramethylbenzene, and the resultant mixture was added dropwise to the above-produced carbon disulfide solution, followed by continuous stirring at room temperature. As the result, a brown to reddish brown solution was produced. After 2 hours of stirring, the solution was allowed to react for another 2 hours under refluxing with the result that the solution turned orange in color.

The resultant reaction mixture was brought back to room temperature and thereafter, was poured onto the mixture of 500 g of water and 500 mL of concentrated hydrochloric acid, followed by stirring for about one hour. Then, the resultant product was subjected to extraction and separation twice with 400 mL each of ether, further with 200 mL each of ether twice. The ether phases thus produced were combined together, and dried with calcium chloride anhydride as the drying agent. After filtering away the used drying agent, the ether was distilled away and the brown viscous solid thus obtained was dissolved in hexane to recrystallize the solid therefrom. The procedure of allowing the solution saturated at room temperature to stand at −20° C. and collecting the precipitate by means of filtration was repeated to afford 75.9 g of 2,3,4,5,6,7-hexamethylindane-1-one as a reddish yellow solid.

(2) Synthesis of 1,2,3,4,5,6,7-heptamethylindene 2,3,4,5,6,7-Hexamethylindane-1-one in an amount of 37.3 g (172 mmol) was dissolved in 200 mL of dehydrated ether (distilled on metallic sodium), and to the resultant solution was added dropwise 120 mL of a 1.4M solution of methyllithium in ether under ice-cooling. After one hour from the addition, the solution turned from reddish brown to reddish yellow and further to clear yellow, was brought back to room temperature and was allowed to react for one hour and for additional 2 hours, under heating refluxing to complete the reaction. The reaction product was quenched under ice-cooling with 20 mL of water and then with 150 mL of 1N aqueous solution of ammonium chloride to separate the organic phase. The separated organic phase was subjected to extraction and separation twice repeatedly with 100 mL each of ether, and the organic phases thus produced were combined together, washed with saturated aqueous solution of sodium chloride and was dried with magnesium sulfate anhydride as the drying agent. After the used drying agent was filtered away, the ether solution was subjected to dehydration reaction by incorporating with small pieces of iodine in an atmosphere of nitrogen for replacing, allowed to stand overnight in an atmosphere of nitrogen, and was subjected to heating refluxing for 3 hours to complete the reaction. The reaction product thus obtained was washed twice with 150 mL each of 0.2N aqueous solution of sodium hydrosulfite and twice with 150 mL each of saturated aqueous solution of sodium chloride, and dried with magnesium sulfate anhydride as the drying agent.

Subsequently, by filtering away the used drying agent and distilling away the ether, there was produced brown crude 1,2,3,4,5,6,7-heptamethylindene, which was dissolved again in 300 mL of hexane and dried with magnesium sulfate anhydride as the drying agent to afford a yellow solution. Then, by filtering away the used drying agent and distilling away the hexane, there was produced an orange-colored oil, which was adsorbed onto 100 g of silica-gel column and eluted with hexane to afford 24.3 g (113 mmol) of objective 1,2,3,4,5,6,7-heptamethylindene in the form of yellow solid in a yield rate of 65.7%.

(3) Synthesis of 1,2,3,4,5,6,7-heptamethylindenyltrimethylsilane 1,2,3,4,5,6,7-Heptamethylindene in an amount of 24.3 g (113 mmol) was dissolved in 150 mL of dried hexane, to the resultant solution was added 1 mL of hexamethyl phosphoamide (HMPA), and to the mixture thus formed was added dropwise, under ice-cooling, 80 mL of a 1.7M solution of tert-butyllithium in pentane. After 2 hours from the addition, 1,2,3,4,5,6,7-heptamethylindenyllithium thus produced was settled, subjected to decantation for separating the solution and washed three times with 100 mL each of hexane to afford yellowish white solid. The solid thus obtained was dissolved in 150 mL of dehydrated tetrahydrofuran (THF) to form a red solution, which was incorporated under ice-cooling with 13.0 g (120 mmol, 15.2 mL) of trimethylchlorosilane (TMSCl) that had been subjected to simple distillation, was brought back to room temperature and was allowed to stand overnight.

The yellow solution thus obtained was incorporated with 20 mL of water for quenching and THF was removed under reduced pressure. Then, the solution was extracted and separated with 500 mL of hexane, the organic phase thus obtained was dried with magnesium sulfate anhydride as the drying agent, the used drying agent was filtered away, and the volatile components were distilled away under reduced pressure. As the result, there was produced 1,2,3,4,5,6,7-heptamethylindenyltrimethylsilane in the form of yellowish white solid in a yield of 19.5 g (62.2 mmol) and in a yield rate of 55%.

The product was analyzed by $^1$H-NMR by the use of trimethylsilane as the standard and heavy chloroform (CDCl$_3$) as the solvent with the results as follows:

$^1$H-NMR: 2.60 ppm (3H, s), 2.40 ppm (3H, s), 2.33 ppm (3H, s), 2.31 ppm (3H, s), 2.28 ppm (3H, s), 1.99 ppm (3H, s), 1.64 ppm (3H, s), −0.09 ppm (9H, s)

(4) Synthesis of 1,2,3,4,5,6,7-heptamethylindenyltitanium trichloride

Titanium tetrachloride in an amount of 15.2 g (80 mmol, 8.8 mL) was dissolved in 100 mL of dehydrated toluene, and to the resultant solution was added dropwise, at room temperature, a solution of 19.52 g of 1,2,3,4,5,6,7-heptamethylindenyltrimethylsilane in 150 mL of toluene over a period of 3 hours. After one hour of heating refluxing of the mixed solution thus obtained, there was produced a toluene-soluble portion at 80° C., which then was extracted twice with 100 mL each of toluene. By filtering off the toluene-insoluble portion, there was obtained a green toluene solution, and the volatile components of which were distilled away at 40° C. under reduced pressure to afford dark green solid. Thereafter, the solid was incorporated with 20 mL of toluene and then with 200 mL of hexane, and the insoluble portion was collected by filtration as the objective product in a yield of 9.43 g (26 mmol) and in a yield rate of 39%. The product was slightly soluble in boiling hexane, readily soluble in toluene, and was analyzed by NMR with the results as follows:

$^1$H-NMR (tetramethylsilane as the standard and heavy chloroform (CDCl$_3$) as the solvent); 2.90 ppm (6H, s), 2.68 ppm (6H, s), 2.46 ppm (3H, s), 2.38 ppm (6H, s), $^{49}$Ti-NMR (titanium tetrachloride as the standard and CDCl$_3$ as the solvent); 19.55 ppm.

The schematic synthesis process for compound A is illustrated as follows:

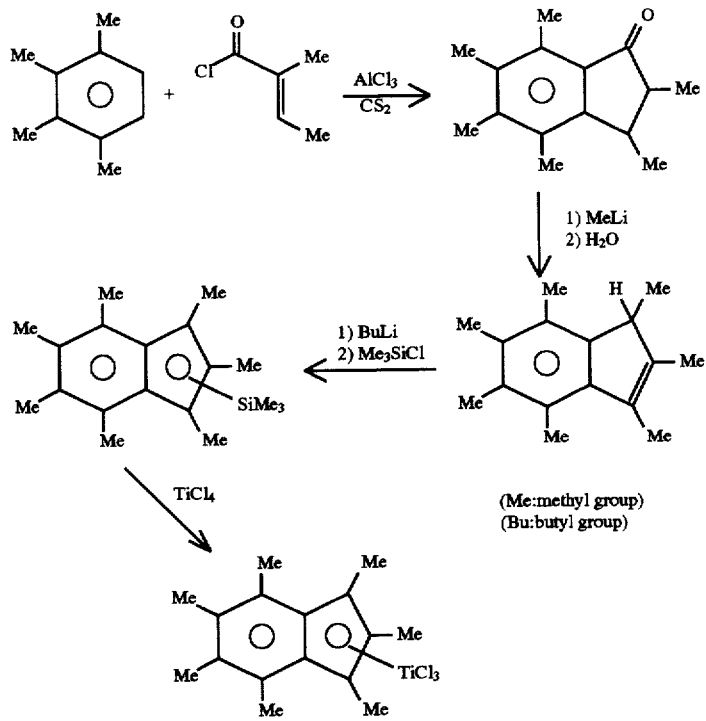

(Me:methyl group)
(Bu:butyl group)

Synthesis Example 2

Synthesis of 1,2,3,4,5,6,7-heptamethylindenylmethyltitanium trimethoxide (compound B)

1.48 g (4 mmol) of 1,2,3,4,5,6,7-heptamethylindenyltitanium trichloride which had been synthesized in Synthesis Example 1 was dissolved in 20 mL of dehydrated toluene in an atmosphere of nitrogen, and to the resultant solution were added, under ice-cooling, 0.64 g (20 mmol, 0.8 mL) of dehydrated methanol and then 2.03 g (20 mmol, 2.8 mL) of dehydrated triethylamine. After 30 minutes from the addition, the mixture was brought back to room temperature and stirred overnight. Subsequently, the volatile components in the mixture were distilled away at room temperature under reduced pressure, the nonvolatile portion was extracted by adding thereto 80 mL of dried hexane, and the hexane-insoluble portion was removed with a glass filter. By distilling away the remaining hexane from the resultant yellow filtrate under reduced pressure, there was obtained the title compound in the form of red solid in a yield of 1.30 g (4 mmol) and in a yield rate of 100%.

The product was analyzed by $^1$H-NMR by the use of tetramethylsilane as the standard and CDCl$_3$ as the solvent with the results as follows: $^1$H-NMR; 2.45 ppm (6H, s), 2.46 ppm (6H, s), 2.20 ppm (6H, s), 2.04 ppm (3H, s), 0.614 ppm (6H, s).

Synthesis Example 3

Synthesis of 1,2,4,5,6,7-hexamethylindenyltitanium trichloride (Compound C)

(1) Synthesis of 1,2,4,5,6,7-Hexamethylindene

Lithium aluminum hydride (LAH) in an amount of 3.09 g (81 mmol) was suspended in dried ether (distilled on metallic sodium). 38.7 g (180 mmol) of 2,3,4,5,6,7-hexamethylindane-1-one which had been synthesized in Synthesis Example 1 was dissolved in 200 mL of dried ether, and the resultant ether solution was added dropwise to the above-prepared suspension of LAH at a rate causing mild reflux. The dropwise addition was completed over a period of 1.5 hour, and thereafter stirring was continued for 2.5 hours under heating refluxing. The reaction product was quenched under ice-cooling with 20 mL of water and then with 200 mL of 1N aqueous solution of ammonium chloride to separate the organic phase. The separated organic phase was subjected to extraction and separation twice repeatedly with 100 mL each of ether, and the organic phases thus produced were combined together, washed with saturated aqueous solution of sodium chloride and was dried with magnesium sulfate anhydride as the drying agent. After the used drying agent was filtered away, the ether solution was subjected to dehydration reaction by incorporating with small pieces of iodine in an atmosphere of nitrogen for replacing, allowed to stand overnight in an atmosphere of nitrogen, and was subjected to heating refluxing for 3 hours to complete the reaction. The reaction product thus obtained was washed twice with 150 mL each of 0.2N aqueous solution of sodium hydrosulfite and twice with 150 mL each of saturated aqueous solution of sodium chloride, and dried with magnesium sulfate anhydride as the drying agent.

Subsequently, by filtering away the used drying agent and distilling away the ether, there was produced yellow crude 1,2,4,5,6,7-hexamethylindene, which was dissolved again in 300 mL of hexane and dried with magnesium sulfate anhydride as the drying agent to afford a yellow solution. Then, by filtering away the used drying agent and distilling away the hexane, there was produced a yellow solid, the solution of which in hexane, was adsorbed onto 20 g of silica-gel. The resultant slurry in hexane was developed in 80 g of silica-gel column and eluted with hexane to afford 28.8 g (144 mmol) of objective 1,2,4,5,6,7-hexamethylindene in the form of yellowish white solid in a yield rate of 80.4%.

(2) Synthesis of 1,2,4,5,6,7-hexamethylindenyltrimethylsilane 1,2,4,5,6,7-Hexamethylindene in an amount of 14.4 g (72 mmol) was dissolved in 150 mL of dried hexane, to the resultant solution was added 0.5 mL of hexamethyl phosphoamide (HMPA), and to the mixture thus formed was added dropwise 47 mL of a 1.7M solution of tert-butyllithium in pentane. After 2 hours from the addition, 1,2,4,5,6,7-hexamethylindenyllithium thus produced was settled, subjected to decantation for separating the solution and washed three times with 100 mL each of hexane to afford yellowish white solid. The solid thus obtained was dissolved in 100 mL of dehydrated tetrahydrofuran (THF) to form a red solution, which was incorporated under ice-cooling with 8.7 g (80 mmol, 10.2 mL) of trimethylchlorosilane (TMSCl) that had been subjected to simple distillation, was brought back to room temperature and was allowed to stand overnight.

The yellow solution thus obtained was incorporated with 20 mL of water for quenching and THF was removed under reduced pressure. Then the solution was extracted and separated with 500 mL of hexane, the organic phase thus obtained was dried with magnesium sulfate as the drying agent, the used drying agent was filtered away, and the volatile components were distilled away under reduced pressure. As the result, there was produced 1,2,4,5,6,7-hexamethylindenyltrimethylsilane in the form of yellow solid in a yield of 18.0 g (60.4 mmol) and in a yield rate of 84%.

(3) Synthesis of 1,2,4,5,6,7-hexamethylindenyltitanium trichloride

Titanium tetrachloride in an amount of 15.2 g (80 mmol, 8.8 mL) was dissolved in 100 mL of dehydrated toluene, and to the resultant solution was added dropwise, at room temperature, a solution of 18.02 g of 1,2,4,5,6,7-hexamethylindenyltrimethylsilane in 150 mL of toluene over a period of 3 hours. After one hour of heating refluxing of the mixed solution thus obtained, there was produced a toluene-soluble portion at 80° C., which then was extracted twice with 100 mL each of toluene. By filtering off the toluene-insoluble portion, there was obtained a green toluene solution, and the volatile components of which were distilled away at 40° C. under reduced pressure to afford dark green solid. Thereafter, the solid was incorporated with 20 mL of toluene and then with 200 mL of hexane, and the insoluble portion was collected by filtration. The insoluble portion was subjected to Soxhlet extraction by using boiling hexane to recover the title complex at 88% recovery rate from the extract solution in a yield of 21.07 g (60 mmol) and in a yield rate of 75%. The product was readily soluble in toluene, and was analyzed by NMR with the results as follows: $^1$H-NMR(tetramethylsilane as the standard and heavy chloroform (CDCl$_3$) as the solvent); 6.89 ppm (3H, s), 2.86 ppm (3H, s), 2.68 ppm (3H, s), 2.53 ppm (3H, s), 2.47 ppm (3H, s), 2.37 ppm (3H, s), 2.35 ppm (3H, s), $^{49}$Ti-NMR (titanium tetrachloride as the standard and CDCl$_3$ as the solvent); −75.54 ppm.

The schematic synthesis process for compound C is illustrated as follows;

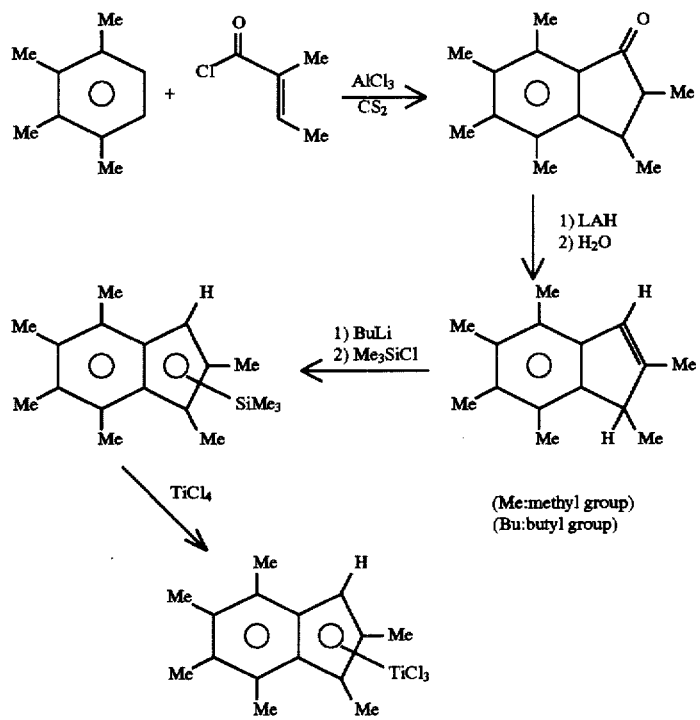

(Me:methyl group)
(Bu:butyl group)

Synthesis Example 4

Synthesis of 1,2,4,5,6,7-hexamethylindenyltrimethyltitanium (Compound D)

1,2,4,5,6,7-Hexamethylindenyltitanium trichloride in an amount of 0.88 g (2.5 mmol) which had been synthesized in Synthesis Example 3 was dissolved in 50 mL of dehydrated THF in an atmosphere of nitrogen. The resultant solution was incorporated at −78° C. with 9.0 mL of 1.0M solution of methylmagnesium bromide in THF, and after the elapse of 15 minutes was gradually brought back to room temperature, with the result that the solution turned to yellowish brown gradually. After the elapse of 15 minutes, the volatile components in the solution were distilled away under reduced pressure to leave only the bone-dried matter, which was extracted with a total quantity of 250 mL of dried hexane. The hexane-insoluble portion was filtered off, and the volatile components in the filtrate solution were distilled away to afford a brown oil in a yield of 0.62 g (2.1 mmol) and in a yield rate of 85%. The oil was allowed to stand overnight in a refrigerator with the result that the oil turned to a brown solid.

The resultant solid was analyzed by $^1$H-NMR by the use of tetramethylsilane as the standard and $CDCl_3$ as the solvent with the results as follows:

$^1$H-NMR; 6.23 ppm (1H, s), 2.52 ppm (3H, s), 2.47 ppm (3H, s), 2.26 ppm (3H, s), 2.21 ppm (3H, s), 2.20 ppm (3H, s), 2.14 ppm (3H, s), 0.65 ppm (9H, s).

Synthesis Example 5

Synthesis of 1,2,3,-trimethylindenyltitanium trichloride (Compound E)

(1) Synthesis of 2,3,-dimethylindane-1-one

Aluminum trichloride in an amount of 30.7 g (250 mmol) was suspended in 150 mL of dried carbon disulfide (dried and distilled on calcium hydride) and was brought to an ice-cooling temperature. Then, 25.1 g (212 mmol) of tigloyl chloride was mixed with 16.6 g (212 mmol) of benzene, and to the resultant mixture was added dropwise the above-produced carbon disulfide solution, followed by continuous stirring at room temperature. As the result, a yellow solution was gradually produced. The solution was allowed to stand overnight, with the result that the solution was separated into two phases including a brown phase and a colorless phase. The solution was allowed to react for another 5 hours under refluxing. The resultant reaction mixture was brought back to room temperature and thereafter, was poured onto the mixture of 250 g of water and 250 mL of concentrated hydrochloric acid, followed by stirring for about one hour. Then, the resultant product was subjected to extraction and separation four times repeatedly with 200 mL each of ether. The ether phases thus produced were combined together, and dried with calcium chloride anhydride as the drying agent. After filtering away the used drying agent, the ether was distilled away and the brown viscous oil was obtained. Because of its being readily soluble in hexane, the oil was again dissolved in hexane, and the resultant solution was washed twice with 150 mL each of saturated aqueous solution of sodium carbonate and twice with 150 mL each of saturated aqueous solution of sodium chloride, and dried with magnesium sulfate anhydride. By distilling away the hexane, there was obtained 19.9 g of 2,3-dimethylindane-1-one.

(2) Synthesis of 1,2,3-trimethylindene 2,3-dimethylindane-1-one in an amount of 19.2 g (124 mmol) was dissolved in 100 mL of dehydrated ether (distilled on metallic sodium) and to the resultant solution was added dropwise 100 mL of a 1.4M solution of methyllithium in ether under ice-cooling. After one hour from the addition, the solution turned to violet color, was brought back to room temperature and was allowed to react for 2 hours under heating refluxing to complete the reaction. The reaction product was quenched under ice-cooling with 20 mL of water and then with 100 mL of 1N aqueous solution of ammonium chloride to separate the organic phase. The separated organic phase was subjected to extraction and separation twice repeatedly with 100 mL each of ether and the organic phases thus produced were combined together, washed with saturated aqueous solution of sodium chloride and was dried with magnesium sulfate anhydride as the drying agent. After the used drying agent was filtered away, the ether solution was subjected to dehydration reaction by incorporating with small pieces of iodine in an atmosphere of nitrogen for replacing, allowed to stand overnight in an atmosphere of nitrogen, and was subjected to heating refluxing for 3 hours to complete the reaction. The reaction product thus obtained was washed twice with 150 mL each of 0.2N aqueous solution of sodium hydrosulfite and twice with 150 mL each of saturated aqueous solution of sodium chloride, and dried with magnesium sulfate anhydride as the drying agent.

Subsequently, by filtering away the used drying agent and distilling away the ether, there was produced brown crude 1,2,3,-trimethylindene, which was dissolved again in 200 mL of hexane and dried with magnesium sulfate anhydride as the drying agent to afford a brown solution. Then, by filtering away the used drying agent and distilling away the hexane, there was produced an brown-colored oil, the solution of which in hexane was adsorbed onto 20 g of silica-gel column. The adsorbed oil in 80 g of silica-gel was eluted with hexane to afford the objective 1,2,3,-trimethylindene in the form of orange-colored oil in a yield of 4.09 g and in a yield rate of 20.8%.

(3) Synthesis of 1,2,3-trimethylindenyltrimethylsilane 1,2,3-Trimethylindene in an amount of 4.09 g (26 mmol) was dissolved in 100 mL of dried THF, and to the resultant solution was added dropwise, under ice-cooling 19 mL of a 1.7M solution of tert-butyllithium in pentane. After 2 hours of reaction at room temperature, the reaction product was incorporated under ice-cooling with 3.25 g (30 mmol, 3.8 mL) of trimethylchlorosilane (TMSCl) that had been subjected to simple distillation, was brought back to room temperature and was allowed to stand overnight. The yellow solution thus obtained was incorporated with 20 mL of water for quenching and THF was removed under reduced pressure. Then, the solution was extracted and separated with 300 mL of hexane, the organic phase thus obtained was dried with magnesium sulfate anhydride as the drying agent, the used drying agent was filtered away, and the volatile components were distilled away under reduced pressure. As the result, there was produced 1,2,3-trimethylindenyltrimethylsilane in the form of yellow oil in a yield of 4.27 g (18.5 mmol) and in a yield rate of 72%.

The product was analyzed by $^1$H-NMR by the use of trimethylsilane as the standard and heavy chloroform ($CDCl_3$) as the solvent with the results as follows: $^1$H-NMR; 7.25 to 7.04 ppm (4H, m), 2.03 ppm (3H, s), 1.93 ppm (3H, s), 1.38 ppm (3H, s), −0.20 ppm (9H, s).

(4) Synthesis of 1,2,3,-trimethylindenyltitanium trichloride

Titanium tetrachloride in an amount of 4.7 g (25 mmol, 2.7 mL) was dissolved in 80 mL of dehydrated toluene, and to the resultant solution was added dropwise, at room temperature, a solution of 4.27 g of 1,2,3, trimethylindenyl-trimethylsilane in 40 mL of toluene over a period of 3 hours.

After one hour of heating refluxing of the mixed solution thus obtained, there was produced a toluene-soluble portion at 80° C., which then was extracted twice with 100 mL each of toluene. By filtering off the toluene-insoluble portion with a filter, there was obtained a green toluene solution, and the volatile components of which were distilled away at 40° C. under reduced pressure to afford dark green solid. Thereafter, the solid was incorporated with 20 mL of toluene and then with 200 mL of hexane, and the insoluble portion was collected by filtration as the objective product. Further, a slight amount of decomposed product was removed with boiling hexane. The final product was obtained in a yield of 4.7 g (14.5 mmol) and in a yield rate of 58%, and was analyzed by NMR with the results as follows: $^1$H-NMR (Tetramethylsilane as the standard and $CDCl_3$ as the solvent); 7.49 to 7.75 ppm (4H, dq), 2.72 ppm (6H, s), 2.53 ppm (3H, s), $^1$H-NMR (tetramethylsilane as the standard and heavy benzene as the solvent); 7.27 to 6.89 ppm (4H, dq), 2.23 ppm (6H, s), 1.96 ppm (3H, s).

The schematic synthesis process for compound E is illustrated as follows.

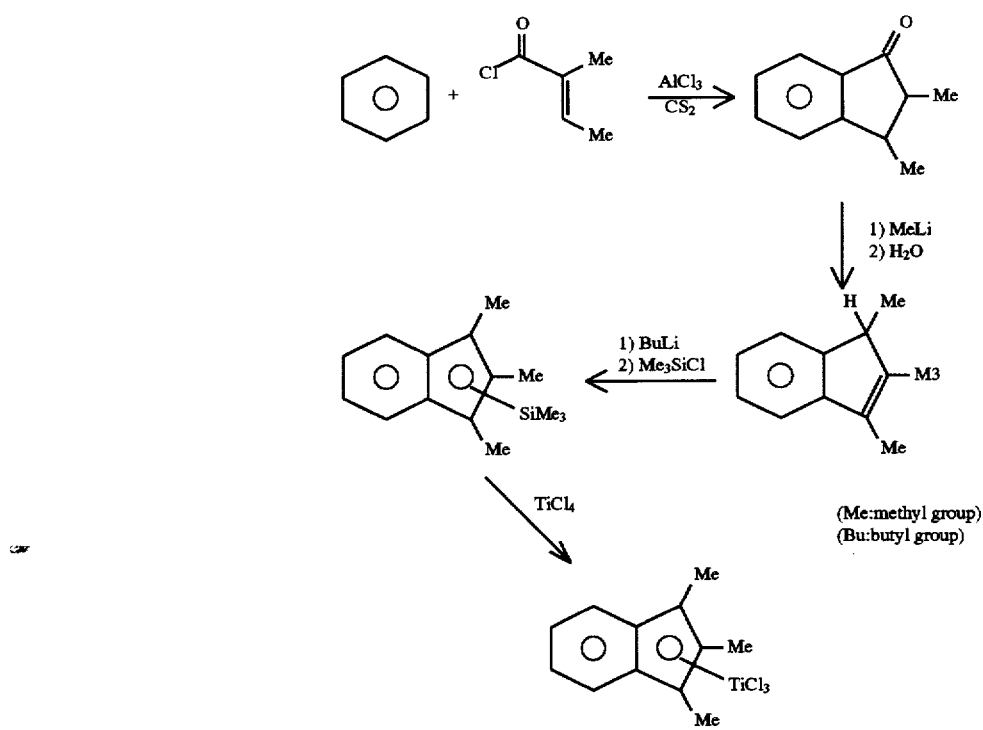

In addition, the foregoing (3) 1,2,3-trimethylindenyltrimethylsilane can be synthesized through the process illustrated by the following schematic synthesis process.

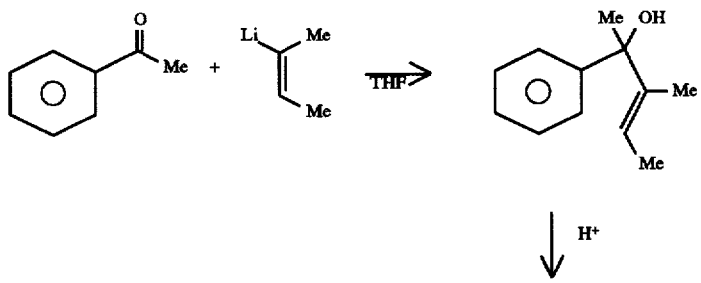

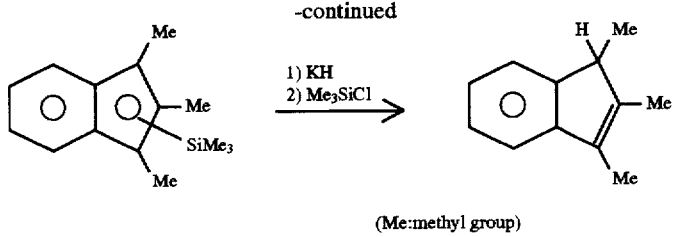

(Me:methyl group)

Synthesis Example 6

Synthesis of 1,2,3-trimethylindenyltrimethyltitanium (Compound F)

1,2,3-trimethylindenyltitanium trichloride in an amount of 0.81 g (2.5 mmol) which had been synthesized in Synthesis Example 5 was dissolved in 50 mL of dehydrated THF in an atmosphere of nitrogen. The resultant solution was incorporated under ice-cooling, with 9.0 mL of 1.0M solution of methylmagnesium bromide in THF, and after the elapse of 15 minutes was gradually brought back to room temperature, with the result that the solution turned to yellowish brown gradually. After the elapse of 30 minutes, the volatile components in the solution were distilled away under reduced pressure to leave only the bone-dried matter, which was extracted with a total quantity of 250 mL of dried hexane. The hexane-insoluble portion was filtered off, and the volatile components in the filtrate solution were distilled away to afford a reddish yellow oil in a yield of 0.59 g (2.3 mmol) and in a yield rate of 90%. The oil was allowed to stand overnight in a refrigerator with the result that the oil turned to a yellow solid.

EXAMPLE 1

In a 30 mL glass ampule which had been dried and purged with nitrogen were placed 10 mL of styrene, 62.5 µL of 2 mol/L solution of triisobutylaluminum in toluene and 125 µL of 1 mol/L solution of aluminoxane in toluene, followed by sealing the ampule with a teflon cap, then the ampule was immersed in an oil bath at 70° C. and allowed to stand for 15 minutes. Then, to the resultant mixture was added 125 µL of 10 mmol/L of the Compound A which had been synthesized in Synthesis Example 1 in toluene to proceed with polymerization at 70° C. for 4 hours. After the completion of the reaction, the content in the ampule was washed with methanol and dried to recover 0.75 g of polymer. The polymer was subjected to Soxhlet extraction for 5 hours by the use of boiling methyl ethyl ketone to produce 0.38 g of syndiotactic polystyrene from the insoluble portion. The objective syndiotactic polystyrene having an intrinsic viscosity [η] of 0.53 dL/g as measured in trichlorobenzene at 135° C. was obtained in a catalytic activity of 13000 g/g.Ti.

EXAMPLE 2

The procedure in Example 1 was repeated to carry out the polymerization except that there was employed the compound C which had been synthesized in Synthesis Example 3 in place of the compound A. The resultant polymer in an amount of 2.30 g was subjected to Soxhlet extraction for 5 hours by the use of methyl ethyl ketone to produce 1.33 g of syndiotactic polystyrene from the insoluble portion. The objective syndiotactic polystyrene having an intrinsic viscosity [η] of 0.37 dL/g as measured in trichlorobenzene at 135° C. was obtained in a catalytic activity of 39,000 g/g.Ti.

EXAMPLE 3

There was prepared in advance, a catalyst solution by mixing 10 mL of 0.05 mol/L solution of triisobutylaluminum in toluene, 5 mL of 10 mmol/L solution of the compound B which had been synthesized in the Synthesis Example 2 in toluene, 5 mL of 10 mmol/L slurry solution of N,N-dimethylaniliumtetrakis(pentafluorophenyl)borate in toluene and 5 mL of toluene in an atomsphere of nitrogen. Subsequently in a 30 mL glass ampule which had been dried and purged with nitrogen were placed 10 mL of styrene and 5 µL of triisobutylaluminum, followed by sealing the ampule with a teflon cap. Then the content in the ampule was heated to 60° C. and incorporated with 1.25 mL of the above-prepared catalyst solution to proceed with polymerization at 60° C. for 4 hours. After the completion of the reaction, the content in the ampule was washed with methanol and dried to recover 0.60 g of polymer. The polymer was subjected to Soxhlet extraction of 5 hours by the use of boiling methyl ethyl ketone to produce 0.37 g of syndiotactic polystyrene from the insoluble portion. The objective syndiotactic polystyrene having an intrinsic viscosity of 0.62 dL/g as measured in trichlorobenzene at 135° C. was obtained in a catalytic activity of 5,000 g/g Ti.

EXAMPLE 4

The procedure in Example 3 was repeated to carry out the polymerization except that there was employed the compound D which had been synthesized in Synthesis Example 4 in place of the compound B. The resultant polymer in an amount of 4.75 g was subjected to Soxhlet extraction for 5 hours by the use of boiling methyl ethyl ketone to produce 3.94 g of syndiotactic polystyrene from the insoluble portion. The objective syndiotactic polystyrene having an intrinsic viscosity [η] of 0.45 dL/g as measured in trichlorobenzene at 135° C. was obtained in a catalytic activity of 40,000 g/g.Ti.

EXAMPLE 5

The procedure in Example 3 was repeated to carry out the polymerization except that the polymerization temperature was set to 80° C. The resultant polymer in an amount of 0.95 g was subjected to Soxhlet extraction for 5 hours by the use of boiling methyl ethyl ketone to produce 0.43 g of syndiotactic polystyrene from the insoluble portion. The objective syndiotactic polystyrene having an intrinsic viscosity [η] of 0.48 dL/g as measured in trichlorobenzene at 135° C. was obtained in a catalytic activity of 8,000 g/g.Ti.

EXAMPLE 6

The procedure in Example 4 was repeated to carry out the polymerization except that the polymerization temperature was set to 70° C. and 375 µL of the mixed catalyst solution was employed. The resultant polymer in an amount of 1.16 g was subjected to Soxhlet extraction for 5 hours by the use of boiling methyl ethyl ketone to produce 0.78 g of syndiotactic polystyrene from the insoluble portion. The objective syndiotactic polystyrene having an intrinsic viscosity [η] of 0.40 dL/g as measured in trichlorobenzene at 135° C. was obtained in a catalytic activity of 32,500 g/g.Ti.

EXAMPLE 7

There was prepared in advance a catalyst solution by mixing 10 mL of 0.1 mol/L solution of triisobutylaluminum in toluene, 5 mL of 10 mmol/L solution of the compound F which had been synthesized in the Synthesis Example 6 in toluene, 5 mL of 10 mmol/L slurry solution of N,N-dimethylaniliumtetrakis(pentafluorophenyl)borate in toluene and 5 mL of toluene in an atmosphere of nitrogen. Subsequently in a 30 mL glass ampule which had been dried and purged with nitrogen was placed 10 mL of styrene, followed by sealing the ampule with a teflon cap. The content in the ampule was heated to 70° C. and incorporated with 250 µL of the above-prepared mixed catalyst solution to proceed with polymerization at 70° C. for 4 hours. After the completion of the reaction, the content in the ampule was washed with methanol and dried to recover 3.37 g of polymer. The polymer was subjected to Soxhlet extraction for 5 hours by the use of boiling methyl ethyl ketone to produce 3.30 g of syndiotactic polystyrene from the insoluble portion. The objective syndiotactic polystyrene had a weight-average molecular weight of 1,100,000 and a molecular-weight distribution of 2.1 and was obtained in a catalytic activity of 139,000 g/g Ti.

INDUSTRIAL APPLICABILITY

The catalyst for producing a styrenic polymer according to the present invention, which comprises a transition metal compound having as a π-ligand, an indenyl group bearing at least one substituent group on the side of its five-membered ring, is imparted with a high activity. By the use of the foregoing catalyst, it is made possible to efficiently produce a styrenic polymer having a high degree of syndiotactic configuration in its aromatic vinyl chain.

We claim:

1. A catalyst for producing a styrenic polymer which comprises a transition metal compound having one and only one π-ligand comprising only one indenyl group, said indenyl group bearing a substituent group at at least the 1-, 2-, or 3- positions of the indenyl ring, and wherein the transition metal is at least one metal selected from the group consisting of titanium, zirconium, hafnium, niobium and tantalum.

2. A catalyst for producing a styrenic polymer which comprises an (A) transition metal compound having one and only one π-ligand comprising only one indenyl group, said indenyl group bearing a substituent group at at least the 1-, 2-, or 3-positions of the indenyl ring, and wherein the transition metal is at least one metal selected from the group consisting of titanium, zirconium, hafnium, niobium and tantalum, and (B) at least one compound selected from the group consisting of an ① aluminoxane and an ② ionic compound comprising an anion that does not coordinate to the transition metal compound of component (A) in its cationic form, and a cation.

3. A catalyst for producing a styrenic polymer which comprises an (A) transition metal compound having one and only one π-ligand comprising only one indenyl group, said indenyl group bearing a substituent group at at least the 1-, 2-, or 3-positions of the indenyl ring, and wherein the transition metal is at least one metal selected from the group consisting of titanium, zirconium, hafnium, niobium and tantalum, (B) at least one compound selected from the group consisting of ① an aluminoxane and ② (an ionic compound comprising an anion that does not coordinate to the transition metal compound of component (A) in its cationic form, and a cation, and (C) a Lewis acid.

4. A process for producing a styrenic polymer which comprises polymerizing an (a) styrenic monomer along with (b) at least one compound selected from olefins, diolefins and alkynes in the presence of the catalyst as set forth in claim 2.

5. The catalyst for producing a styrenic polymer according to claim 1, wherein the substituent group is an alkyl group having 1 to 20 carbon atoms.

6. The catalyst for producing a styrenic polymer according to claim 2 wherein said aluminoxane is a chain aluminoxane or a cyclic aluminoxane.

7. A process for producing a styrenic polymer which comprises polymerizing a styrenic monomer in the presence of the catalyst as set forth in claim 1.

8. A process for producing a styrenic polymer which comprises polymerizing a styrenic monomer along with at least one compound selected from olefins, diolefins and alkynes in the presence of the catalyst as set forth in claim 1.

9. A process for producing a styrenic polymer which comprises polymerizing a styrenic monomer in the presence of the catalyst as set forth in claim 3.

10. A process for producing a styrenic polymer which comprises polymerizing an (a) styrenic monomer along with (b) at least one compound selected from olefins, diolefins and alkynes in the presence of the catalyst as set forth in claim 3.

11. The catalyst for producing a styrenic polymer according to claim 2, wherein the substituent group is an alkyl group having 1 to 20 carbon atoms.

12. The catalyst for producing a styrenic polymer according to claim 3, wherein the substituent group is an alkyl group having 1 to 20 carbon atoms.

13. The catalyst for producing a styrenic polymer according to claim 3, wherein said aluminoxane is a chain aluminoxane or a cyclic aluminoxane.

14. A process for producing a styrenic polymer which comprises polymerizing styrenic monomer in the presence of the catalyst as set forth in claim 2.

* * * * *

UNITED STATES PATENT AND TRADEMARK OFFICE
CERTIFICATE OF CORRECTION

PATENT NO. : 5,747,614
DATED      : May 5, 1998
INVENTOR(S): Mizutomo TAKEUCHI, et al.

It is certified that error appears in the above-identified patent and that said Letters Patent is hereby corrected as shown below:

On the title page, Item [87], the PCT Pub. No., is incorrect. It should read:

-- PCT Pub. No.: WO95/01378 --

Item [54], the title, is incorrect. It should read:

-- CATALYST FOR PRODUCING STYRENIC POLYMER AND PROCESS FOR PRODUCING STYRENIC POLYMER BY USING SAME --

Signed and Sealed this

Thirtieth Day of June, 1998

Attest:

BRUCE LEHMAN

*Attesting Officer*    *Commissioner of Patents and Trademarks*